US 6,499,356 B1

(12) United States Patent
Flaud et al.

(10) Patent No.: US 6,499,356 B1
(45) Date of Patent: Dec. 31, 2002

(54) APPARATUS FOR NON-DESTRUCTIVE EXTENSOMETRIC MEASUREMENT OF THE SUPPORT FORCES THAT CAN BE EXERTED BY AN ORTHESIS OF THE ELASTIC HOSE TYPE

(75) Inventors: Patrice Flaud, Combs la Ville (FR); Jean-Louis Counord, Rueil Malmaison (FR)

(73) Assignee: Innothera Topic International, Arcueil (FR)

( * ) Notice: Subject to any disclaimer, the term of this patent is extended or adjusted under 35 U.S.C. 154(b) by 0 days.

(21) Appl. No.: 09/787,441
(22) PCT Filed: Aug. 8, 2000
(86) PCT No.: PCT/FR00/02274
§ 371 (c)(1),
(2), (4) Date: Jun. 25, 2001
(87) PCT Pub. No.: WO01/11337
PCT Pub. Date: Feb. 15, 2001

(30) Foreign Application Priority Data

Aug. 10, 1999 (FR) ............................................. 99/10366

(51) Int. Cl.⁷ ................................................. G01N 3/08
(52) U.S. Cl. ....................................... 73/831; 73/862.42
(58) Field of Search .......................... 73/788, 790, 794, 73/796, 826, 831, 832, 855, 862.391, 862.42

(56) References Cited

U.S. PATENT DOCUMENTS

| 2,175,661 | A | | 10/1939 | Harry |
| 3,503,257 | A | | 3/1970 | Mcelhaney et al. |
| 3,750,291 | A | | 8/1973 | Foreman |
| 4,137,763 | A | | 2/1979 | Swallow |
| 4,491,255 | A | | 6/1985 | Lachapelle |
| 5,593,072 | A | * | 1/1997 | Hester et al. ................ 198/350 |
| 5,703,688 | A | * | 12/1997 | Bell ....................... 250/559.12 |
| 5,776,123 | A | * | 7/1998 | Goerg et al. ................. 116/205 |

FOREIGN PATENT DOCUMENTS

| FR | 2 764 796 A1 | 12/1998 |
| GB | 2 168 156 A | 6/1986 |

* cited by examiner

Primary Examiner—Max Noori
(74) Attorney, Agent, or Firm—Jacobson Holman PLLC

(57) ABSTRACT

An apparatus has a jig suitable for receiving an orthesis engaged thereon, the jig having two elongate branches, an expander cooperating with facing ends of the branches to move them apart from each other transversely to their long dimension, control system for controlling the expander and suitable for moving the branches so that they move apart from each other progressively and in a controlled manner, and sensors distributed along the length of at least one of the branches and suitable for measuring the force applied locally to the branch by the orthesis at the locations of the respective sensors in terms of a component perpendicular to the profile of the branch.

9 Claims, 2 Drawing Sheets

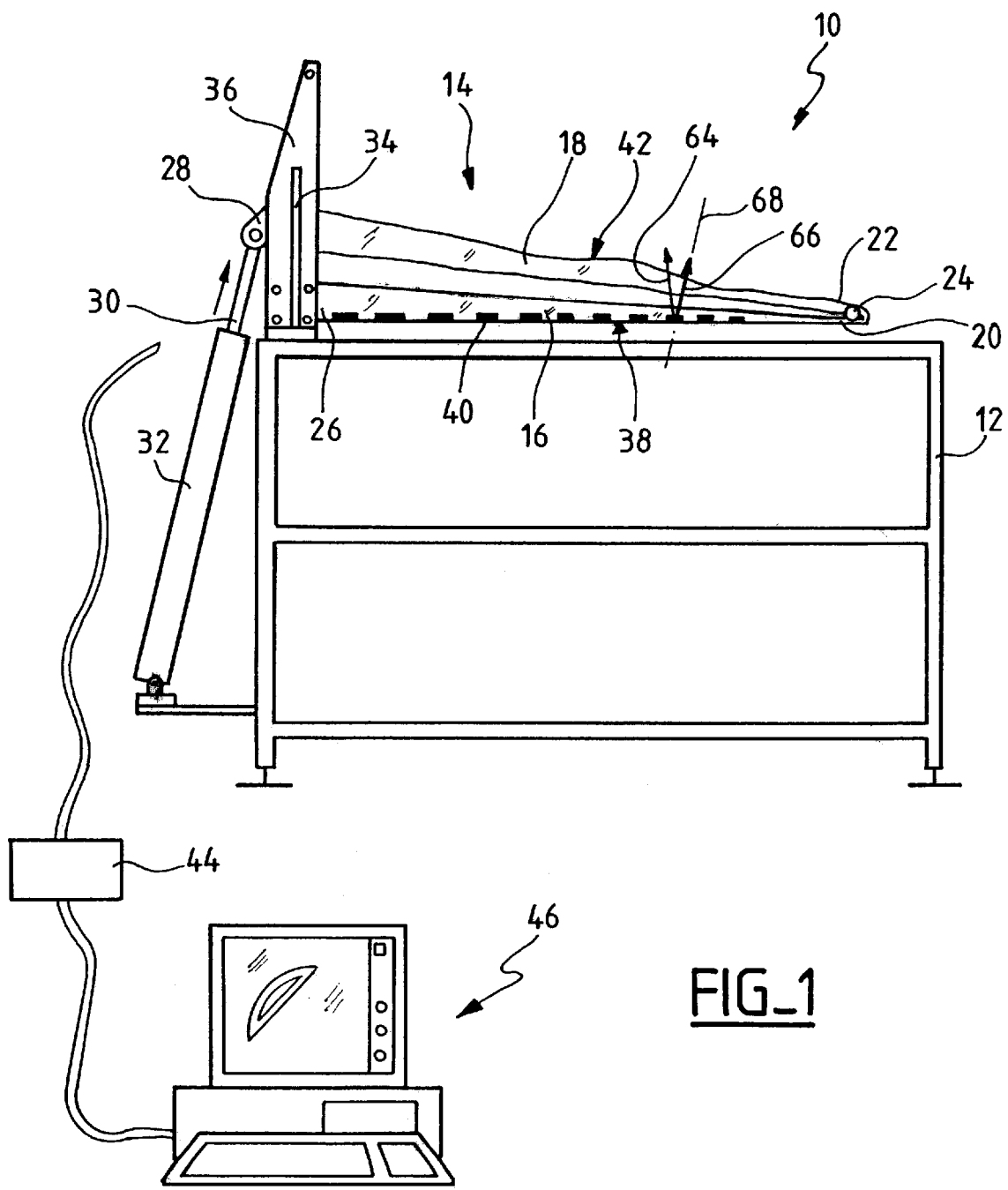
FIG_1

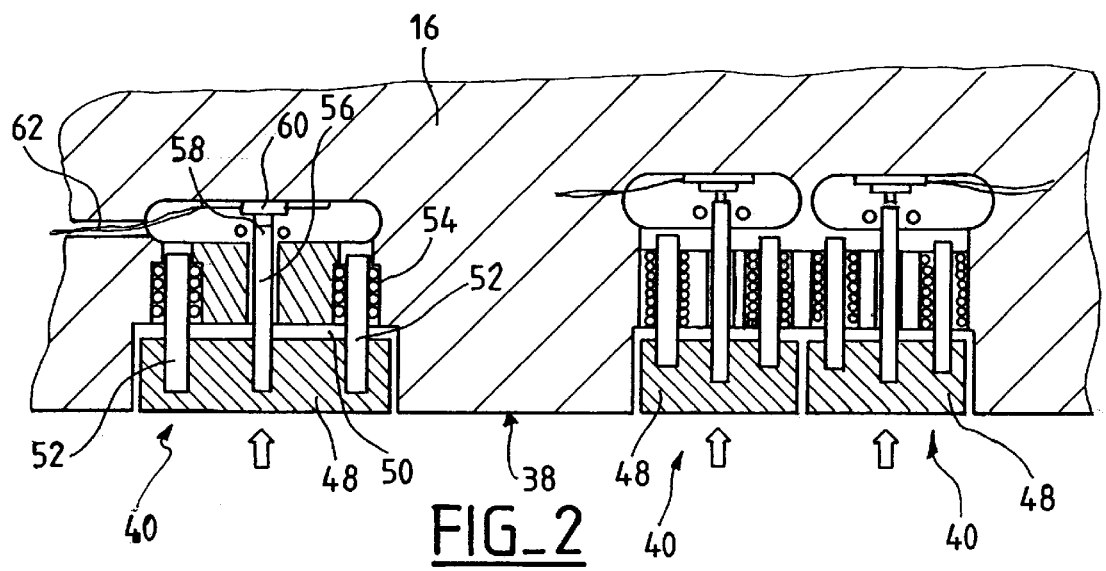
FIG_2
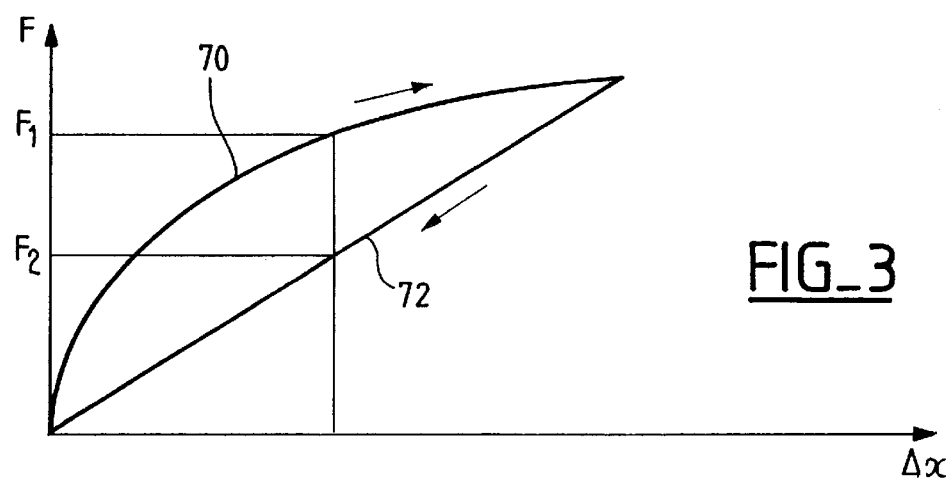
FIG_3
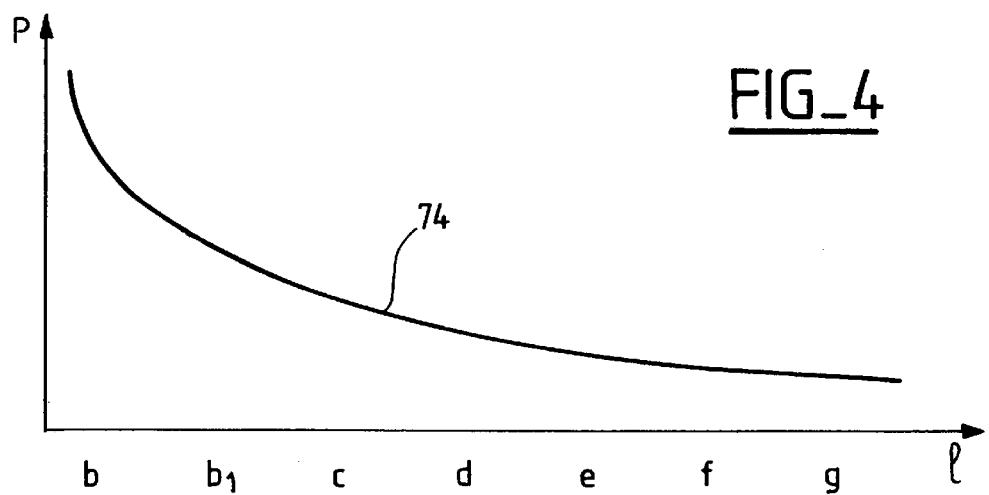
FIG_4

APPARATUS FOR NON-DESTRUCTIVE EXTENSOMETRIC MEASUREMENT OF THE SUPPORT FORCES THAT CAN BE EXERTED BY AN ORTHESIS OF THE ELASTIC HOSE TYPE

This is a 371 of PCT/FR00/02274, filed Aug. 8, 2000.

The invention relates to apparatus for non-destructive extensometric measurement of the support forces that can be exerted by an orthesis of the elastic hose type (where said forces are more exactly both supportive and compressive), the term "elastic hose" being understood broadly, including various kinds of hose such as short socks, socks, thigh-high stockings, self-supporting stockings, tights, maternity tights, men's tights, or half-tights.

The term "extensometric measurement" is used to mean measurement that consists in applying deformation to a precise location of the hose and in measuring the force applied locally by the hose under the effect of said deformation, which force is a function of the elastic characteristics of the materials used and of the structure of the article.

It is necessary to be able accurately and reproducibly to measure the force which a given compressive orthesis can apply, in particular in order to verify that it complies with nominal values specified as a function of a selected class of support.

Such measurement is important particularly during manufacture, in order to verify articles as they come off the knitting machine while performing quality control and optionally adjusting the knitting machine.

Nevertheless, this application is not limiting, and the invention can be used for numerous other purposes, e.g. for testing new materials, developing new products, investigating product fatigue, etc.

Various extensometric measurement apparatuses and protocols have already been proposed for these purposes. However, such methods and apparatuses all present one or more of the following drawbacks:

they are destructive, in particular in systems that use traction claws for imparting forced deformation to the hose;

inspection times are very long: some measurement protocols can take as long as 48 hours, which is incompatible with industrial constraints of the manufacturing quality control type;

the number of measurement points is small, even though the uniformity of hose makes it important to obtain as large as possible a number of measurement points over the entire length of an article;

the equipment is expensive; and multiple jigs need to be provided as a function of the size of the hose or as a function of different hosiery articles, thus requiring a large amount of manipulation.

The object of the present invention is to mitigate all of the above drawbacks by proposing a non-destructive extensometric measurement apparatus that is suitable (amongst other things) for production quality control, because of its robustness, the speed with which it can be used, and its flexibility, including the option of adapting quickly and simply to articles that are different or to different sizes of the same article.

The apparatus of the invention also presents the following advantages:

accurate measurement;

reliable measurement making it possible to provide data reproducibly and independently of the skill of an operator;

measurement that is performed simultaneously at a large number of points;

implementation can be simple and quick;

the data obtained can be digitized, stored, processed, and displayed, in particular for interfacing with computer processing; and it can be used to inspect all of the standard sizes, executions, and lengths currently in production, and also all of the articles that are made to measure.

To this end, the extensometric apparatus of the invention is characterized in that it comprises: a jig suitable for receiving an orthesis engaged thereon, said jig having two elongate branches; expander means cooperating with facing ends of the branches to move them apart from each other transversely to their long dimension; control means for controlling the expander means and suitable for moving the branches so that they move apart from each other progressively and in controlled manner; and sensors distributed along the length of at least one of the branches and suitable for measuring the force applied locally to the branch by the orthesis at the locations of the respective sensors in terms of a component perpendicular to the profile of the branch.

According to various advantageous subsidiary characteristics:

the branches are pivotally united at their ends remote from their ends which co-operate with the expander means, the movement of mutually moving apart from each other being a pivoting movement about the corresponding pivot point;

the sensors include as sensor elements in contact with the orthesis buttons that lie flush with the outside profile of the branch in which they are located;

the expander means comprise a rectilinear branch carrying the sensors and a curvilinear branch whose profile corresponds to that of a leg suitable for receiving the orthesis;

the apparatus includes means for determining the transverse elongation of the orthesis at the location of each of the sensors as a function of the spacing imposed on the branches by the expander means;

the apparatus includes means for recording a plurality of pairs of measurements for each sensor, each pair comprising a force measurement and an elongation measurement, in particular, with means for dynamically determining a force/elongation characteristic; and the apparatus includes means for dynamically determining a force/elongation characteristic.

An embodiment of the invention is described below with reference to the accompanying drawings.

FIG. 1 is a diagrammatic view showing the various elements of the apparatus of the invention.

FIG. 2 is a detail section view showing the structure of the force sensors.

FIG. 3 is a plot of a force/elongation characteristic.

FIG. 4 shows the pressure profile as determined by the apparatus of the invention.

In FIG. 1, overall reference 10 designates the extensometric apparatus of the invention which essentially comprises a frame 12 having a deformable structure 14 mounted thereon for receiving an article of hosiery threaded over its entire length (not including the foot).

The deformable structure 14 comprises two branches or "half-legs" 16, 18 comprising a stationary bottom branch 16 and a moving top branch 18, the two branches being hinged to each other at their respective ends 20, 22 about a common pivot 24 like the two legs of a pair of compasses.

At their opposite ends 26, 28, the branches 16, 18 are connected to expander means for moving them apart from each other in relative pivoting motion about the pivot 24, with this spacing apart from each other being performed, for example, by keeping the end 26 of the bottom branch 16 stationary while moving the end 24 of the top branch 18 by means of the rod 30 of an actuator 32, e.g. an electrical actuator that is programmable in speed and in amplitude. By way of example, the electrical actuator can be based on a stepper motor whose speed is adjustable typically over the range 0 to 500 millimeters per minute (mm/min) and which is capable of providing an opening of amplitude lying in the range 0 to 400 mm between the two arms 16, 18 of the deformable structure 14.

The movement of the moving end 28 is guided by a slot 34 in a vertical slideway 36.

The outside surface of the bottom branch 16 is rectilinear in profile, said branch being provided with a plurality of force sensors 40 that are distributed along the branch 16 at selected points.

The outside profile 42 of the top branch 18 is curvilinear, corresponding to the general shape of a leg.

To enable articles of different sizes and of different kinds to be measured, the top branch 18 can be interchanged with other, similar branches having profiles 42 that are different. In addition, the pivot point 24 can be adapted, e.g. by raising the pivot point for hose sizes of greater diameter.

By way of example, there can be twelve sensors 40 disposed along the bottom branch 16 so as to correspond to the distribution of measuring points known as the "Hohenstein standard", for the points b, b1, c, d, e, f, and a of the standard. Advantageously, the sensors at points c, d, e, f, and a are duplicated, thus giving a total of twelve sensors for seven measurement points. Depending on the article under consideration, only a fraction of the sensors need be used, for example the sensors at points b and b1 for short socks, those at points b, b1, and c, for stockings, those at points b, b1, c, d, e, and f for thigh-high stockings, and all of the sensors for tights.

In order to ensure that the measurements correspond properly with the hosiery points as defined in the Hohenstein standard, it is important to position the hose longitudinally accurately on the jig 14, typically with accuracy of ±3 mm, with measurements being taken from the heel line (the last turn of weft before reaching the heel), which is placed on a suitable marker etched in the branches 16 and 18.

The various sensors 40 determine the force applied by the hose against the surface 38, and the measured values are transmitted via an interface 44 to a microcomputer 46 that serves to process, store, and display the collected data.

FIG. 2 shows one of the sensors 40 in detail.

A measuring button 48, typically having a length of 30 mm in a single sensor (to the left in FIG. 2) and of 2×20 mm for a dual sensor (to the right in FIG. 2), is received in a cavity 50 of the bottom branch 16, the surface of the button lying flush with the outside profile 38 of said bottom branch. To minimize friction, the button 48 is mounted on guides 52 themselves associated with ball bushings 58 so as to permit displacement solely in a direction that is orthogonal to the (rectilinear) profile 38 of the branch 16. The force applied to the button 48 is transmitted by a rod 56 to a finger 58 that comes into contact with a force sensor 60, e.g. a sensor such as the model ELFS6B0-25N-/M1.0,5M/MLL sold under the trademark ENTRAN, which is a strain gauge force sensor having a measurement range of 0 to 25 Newtons (N) in compression, with very low characteristics of non-linearity, drift, hysteresis, etc. The sensor has connection wires 62 (power supply and measurement) running along the bottom branch 16 to the interface 44 with the microcomputer.

The force sensor 60 is associated with a conventional measurement system, and it provides an indication of the force exerted on the flush button 48 by the hose engaged on the extensometer. By taking the ratio of said force divided by the area of the button, it is possible to obtain directly the pressure that is exerted by the hose at this point.

The measurement protocol is as follows.

Initially, both branches 16 and 18 of the extensometer are placed in their position of minimum spacing, and the hose is put onto the extensometer by hand in an unstressed condition, i.e. without any elastic deformation. The leg of the hose is positioned on the extensometer as mentioned above starting from the heel line, with the remainder of the hose then being deployed, still without elastic deformation, over the length of the extensometer (over all or part of said length depending on whether the article is a short sock, a stocking, a pair of tights, etc.). It will be observed that since the extensometer does not have a foot shape at right angles (unlike other known extensometers), putting the hose into place on the apparatus is made that much easier and quicker.

The two branches are then moved apart progressively by means of the actuator 30, 32 and the signals picked up by the sensors 40 are all sent in real time to the computer system which records each of the values. Software calculates the displacement at each inspection point as a function of the amplitude imparted by the actuator.

It will be observed at this stage that the values delivered by each of the sensors must be processed so that the force 64 (FIG. 1) as measured by the sensor perpendicularly to the rectilinear profile 38 of the bottom branch 16 can be converted into the force 66 that is really exerted in the weft line direction 68 of the hose, which is the value that needs to be acquired. To this end, the data acquisition software determines an appropriate correction factor for each measurement point (for each senor) and for each step in the opening of the moving branch 18.

For a given sensor, the force F as a function of the transverse elongation Δx of the hose has the appearance shown in FIG. 3 with a characteristic portion 70 while the branches are opening that is different from the characteristic portion 72 that corresponds to the branches closing (hysteresis effect). To enable the assembly to stabilize, the apparatus is controlled so as to perform a succession of cycles in which the two branches 16 and 18 move apart from and towards each other, with final data acquisition being implemented on the third or the sixth cycle, for example. The number of measurement points during each cycle is typically 500 points for each of the two stages of moving apart and moving together.

It will be observed that data is not acquired simultaneously for each of the measurement points. The beginning of elastic deformation of the hose begins only when the elongation imparted by the extensometer corresponds to the application circumference of the hose, and this is achieved at different spacings for each of the points, so the spacing corresponding to the flat width needs to be taken as a zero reference for each of the points.

Because of hysteresis, a single elongation value can give rise to two different force values F1 and F2; the average can be taken as the measurement value.

On the basis of the data as collected, the software can evaluate various parameters such as:

the support force P at each point;

the stiffness at each point;

the degressivity of each point relative to the ankle; and the degressivity differences between different points.

This data can be displayed, e.g. on a screen, together with parameters such as batch number, test number, and statistical data (standard deviation within a batch), etc.

The force/elongation characteristics (FIG. 3) for each measurement point can be viewed in order to detect anomalies by visual inspection and thus reject measurements that are doubtful.

The apparatus can also display on the screen the pressure profile of the hose under test (FIG. 4) giving values that correspond to the pressures p exerted by the hose as a function of the positions of the various measurement points b, b1, c, . . . as distributed along the length l of the hose.

What is claimed is:

1. Apparatus (1) for non-destructive extensometric measurement of the support forces exerted by an orthesis of the elastic hose type, the apparatus being characterized in that it comprises:

a jig (14) suitable for receiving an orthesis engaged thereon, said jig having two elongate branches (16, 18);

expander means (30, 32) co-operating with facing ends (26, 28) of the branches to move them apart from each other transversely to their long dimension;

control means for controlling the expander means and suitable for moving the branches so that they move apart from each other progressively and in controlled manner; and sensors (40) distributed along the length of at least one of the branches and suitable for measuring the force applied locally to the branch by the orthesis at the locations of the respective sensors in terms of a component perpendicular to the profile of the branch.

2. The apparatus of claim 1, in which the branches are pivotally united at their ends (20, 22) remote from their ends which co-operate with the expander means, the movement of mutually moving apart from each other being a pivoting movement about the corresponding pivot point.

3. The apparatus of claim 1, in which the sensors (40) include as sensor elements in contact with the orthesis buttons (48) that lie flush with the outside profile (48) of the branch in which they are located.

4. The apparatus of claim 1, in which the expander means comprise a rectilinear branch (16) carrying the sensors and a curvilinear branch (18) whose profile corresponds to that of a leg suitable for receiving the orthesis.

5. The apparatus of claim 1, in which the expander means (30, 32) are motorized means.

6. The apparatus of claim 1, including means for determining the transverse elongation ($\Delta x$) of the orthesis at the location of each of the sensors as a function of the spacing imposed on the branches by the expander means.

7. The apparatus of claim 5, including means for recording a plurality of pairs of measurements for each sensor, each pair comprising a force measurement (F) and an elongation measurement ($\Delta x$).

8. The apparatus of claim 1, including means for determining the support pressure profile (P) exerted by the orthesis over the length (2) thereof.

9. The apparatus of claim 4 in combination with means for determining the transverse elongation ($\Delta x$) of the orthesis at the location of each of the sensors as a function of the spacing imposed on the branches by the expander means, including means for dynamically determining a force/elongation characteristic.

* * * * *